United States Patent [19]

Kaneko et al.

[11] Patent Number: 4,694,088
[45] Date of Patent: Sep. 15, 1987

[54] FLUORAN COMPOUNDS

[75] Inventors: Kazuo Kaneko; Susumu Suzuka; Michihiro Gonda; Mikiko Kanasugi, all of Tokyo, Japan

[73] Assignee: Hodogaya Chemical Co., Ltd., Tokyo, Japan

[21] Appl. No.: 807,037

[22] PCT Filed: Mar. 12, 1985

[86] PCT No.: PCT/JP85/00121
§ 371 Date: Nov. 25, 1985
§ 102(e) Date: Nov. 25, 1985

[87] PCT Pub. No.: WO85/04414
PCT Pub. Date: Oct. 10, 1985

[30] Foreign Application Priority Data

Mar. 24, 1984 [JP] Japan ................... 59-55284

[51] Int. Cl.$^4$ ........................... C07D 493/10
[52] U.S. Cl. ................................. 549/226
[58] Field of Search ........................ 549/226

[56] References Cited

U.S. PATENT DOCUMENTS 4,536,220 8/1985 Kondo et al. ............... 549/226

FOREIGN PATENT DOCUMENTS 0112710 7/1984 European Pat. Off. .
109120 10/1974 Japan .
34909 3/1979 Japan .
133258 7/1984 Japan .
2002801 2/1979 United Kingdom .

Primary Examiner—Norma S. Milestone
Attorney, Agent, or Firm—Oblon, Fisher, Spivak, McClelland, & Maier

[57] ABSTRACT

A fluoran compound represented by general formula (I):

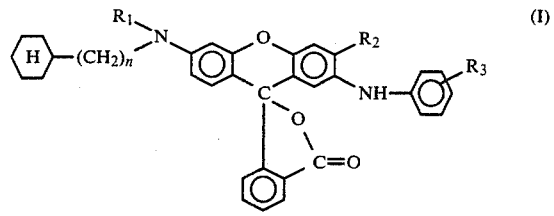

wherein $R_1$ represents a straight or branched alkyl group having 1 to 8 carbon atoms, a cyclohexyl ($C_1$-$C_2$) alkyl group, a cyclohexyl group, a phenyl group which may be substituted by chlorine, an alkoxyalkyl group, a benzyl group which may be substituted by chlorine, or a hydrogen atom;, $R_2$ represents a hydrogen atom, a halogen atom, a lower alkyl group having 1 to 4 carbon atoms, a phenyl group which may be substituted by chlorine, a benzyl group which may be substituted by chlorine, a lower alkoxy group or a lower alkoxyalkyl group; $R_3$ represents a hydrogen atom, a chlorine atom, a fluorine atom or a lower alkyl group having 1 to 4 carbon atoms; and n is 2.

3 Claims, No Drawings

1

FLUORAN COMPOUNDS

FIELD OF THE ART

The present invention relates to novel fluoran compounds. More particularly, the present invention relates to novel fluoran compounds characterized by containing a cyclohexylalkylamino group at the 6-position thereof which are useful as dye precursors used for heat-sensitive recording sheets, heat-sensitive recording sheets by applying an electric current and light-sensitive color forming recording sheets.

BACKGROUND OF THE INVENTION

Known fluoran compounds relating to the present invention are found in Examined Japanese Patent Publication No. 23204/76, No. 29180/76, No. 52759/81 and Unexamined Japanese Patent Publication No. 162690/81. The fluoran compounds disclosed in these gazettes are used as color formers (dye precursors) for heat-sensitive recording sheets, heat-sensitive recording sheets by applying an electric current, pressure-sensitive copying paper, etc.

However, the heat-sensitive recording sheets using these fluoran compounds as color formers requires a high temperature necessary to obtain a color density of 1.0, namely, requires a great consumption energy for attaining a practical color density. In addition, the fluoran compounds encounter disadvantages in moisture resistance, decolorization, oil resistance, resistance to fogging in the background, etc.

DISCLOSURE OF THE INVENTION

As a result of extensive investigations with an attempt to improve the above-described disadvantages, the present inventors have found that novel fluoran compounds having a cyclohexylalkylamino group at the 6-position thereof are colorless or pale color solids in the air but form colors of black hue upon contact with acidic substances and efficiencies as heat-sensitive recording sheets can be markedly improved by the use of these compounds.

That is, the present invention are directed to a fluoran compound represented by the following general formula (I):

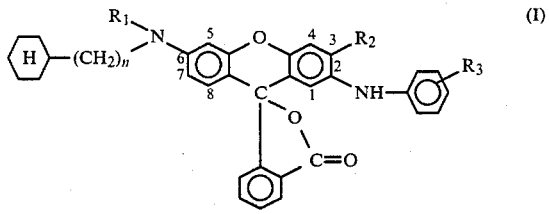

wherein $R_1$ represents a straight or branched alkyl group having 1 to 8 carbon atoms, a cyclohexylalkyl group, a cyclic alkyl group, a phenyl group which may be substituted, an alkoxyalkyl group, a benzyl group which may be substituted or a hydrogen atom; $R_2$ represents a hydrogen atom, a halogen atom, a lower alkyl group having 1 to 4 carbon atoms, a phenyl group which may be substituted, a benzyl group which may be substituted, a lower alkoxy group or a lower alkoxyalkyl group; $R_3$ represents a hydrogen atom, a chlorine atom, a fluorine atom or a lower alkyl group having 1 to 4 carbon atoms; and n represents an integer of 1 to 3, which are characterized by containing a cyclohexylalkylamino group at the 6-position thereof.

The novel fluoran compounds shown by general formula (I) of the present invention may be prepared by the following process.

Diphenylamine derivatives represented by general formula:

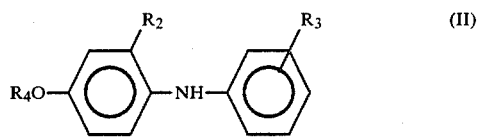

wherein $R_2$ and $R_3$ have the same significances as defined above and $R_4$ represents a hydrogen atom, an acetyl group or a lower alkyl group, are reacted with benzophenone derivatives represented by general formula:

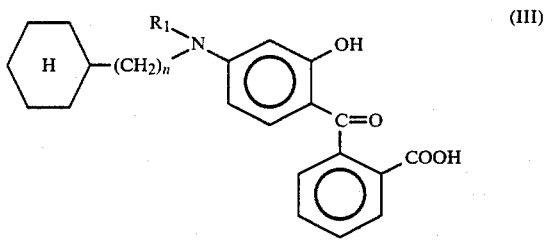

wherein $R_1$ and n have the same significances as defined above, at temperatures of 0° to 80° C. for several hours in the presence of sulfuric acid having a concentration of 80 to 100%. After completion of the reaction, the reaction mixture is poured into water and sodium hydroxide is added thereto to render pH 8 to 10. The precipitates are collected by filtration. Toluene and a 5 to 10% aqueous sodium hydroxide solution are added to the resulting cake. The mixture is stirred under reflux for 1 to 3 hours. The toluene layer is separated by fractionation. After washing with water, the system is concentrated. The precipitated crystals are collected by filtration. By drying the crystals, novel fluoran compounds which are slightly colored can be obtained in high purity and high yield. If necessary, the products are recrystallized from volatile organic solvents such as toluene, acetone, butyl acetate, hexane, etc.

As the condensing agents used in the present invention, there are concentrated sulfuric acid, acetic anhydride, phosphoric acid, polyphosphoric acid, phosphorous oxychloride, zinc chloride, etc. From a viewpoint of preparation, it is preferred to use 80 to 100% sulfuric acid which is a solvent of the benzophenone compounds shown by general formula (III) described above and condensing agent at the same time.

Next, representative examples of the fluoran compounds shown by general formula (I) of the present invention are shown in the table. A color hue indicates the color hue when colored in a silica gel thin layer.

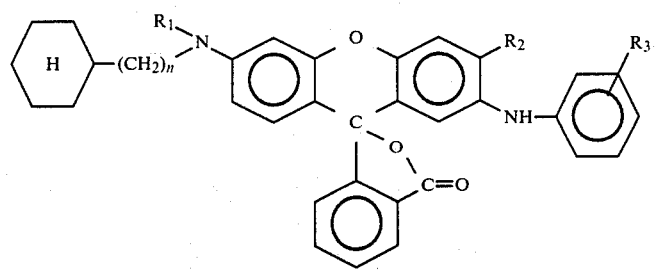

| Compound No. | $R_1$ | $R_2$ | $R_3$ | n | Color Hue |
|---|---|---|---|---|---|
| 1 | $C_2H_5$ | $CH_3$ | H | 1 | reddish black |
| 2 | $CH_3$ | Cl | H | 1 | black |
| 3 | $CH_3$ | H | Cl(o-position) | 1 | reddish black |
| 4 | $CH_3$ | $CH_3$ | H | 2 | reddish black |
| 5 | $CH_3$ | $CH_3$ | H | 1 | reddish black |
| 6 | —CH$_2$—〈cyclohexyl-H〉 | $CH_3$ | H | 1 | reddish black |
| 7 | 〈cyclohexyl-H〉 | $CH_3$ | H | 2 | reddish black |
| 8 | —C$_2$H$_4$—〈cyclohexyl-H〉 | $CH_3$ | H | 2 | reddish black |
| 9 | n-$C_4H_9$ | —$C_2H_4OC_2H_5$ | H | 2 | black |
| 10 | $C_2H_5$ | —CH$_2$—〈phenyl〉 | H | 1 | reddish black |
| 11 | —$CH(CH_3)_2$ | $CH_3$ | H | 1 | reddish black |
| 12 | —$CH(CH_3)_2$ | Cl | H | 2 | reddish black |
| 13 | $C_2H_5$ | H | H | 1 | greenish black |
| 14 | $CH_3$ | —〈phenyl〉 | H | 1 | reddish black |
| 15 | n-$C_4H_9$ | $CH_3$ | H | 1 | reddish black |
| 16 | —CH$_2$—CH$_2$—CH(CH$_3$)CH$_3$ | —$CH_2OC_2H_5$ | H | 1 | black |
| 17 | $C_2H_5$ | $CH_3$ | H | 2 | reddish black |
| 18 | $C_2H_5$ | Cl | H | 2 | black |
| 19 | —$C_2H_4$—〈cyclohexyl-H〉 | Cl | H | 2 | black |
| 20 | $C_2H_5$ | H | Cl | 1 | reddish black |
| 21 | —$CH(CH_3)_2$ | H | Cl | 1 | reddish black |
| 22 | $C_2H_5$ | Cl | H | 1 | black |
| 23 | $CH_3$ | H | F(o-position) | 1 | black |

-continued

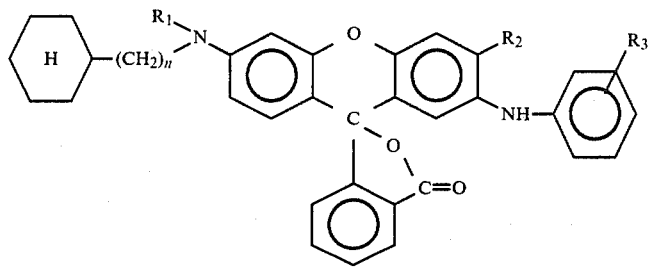

| Compound No. | R$_1$ | R$_2$ | R$_3$ | n | Color Hue |
|---|---|---|---|---|---|
| 24 | —CH$_2$—⟨cyclohexyl-H⟩ | CH$_3$ | H | 2 | reddish black |
| 25 | CH$_3$ | CH$_3$ | H | 3 | reddish black |
| 26 | CH$_3$ | H | CH$_3$ | 1 | reddish black |
| 27 | —⟨C$_6$H$_4$⟩—Cl | CH$_3$ | H | 1 | black |
| 28 | CH$_3$ | OCH$_3$ | H | 1 | black |

Heat-sensitive recording sheets which contain the thus obtained novel fluoran compounds of the present invention as color formers are characterized in that color sensitivity is excellent, the density at the background is small (fogging at the background is minimized), etc.

BEST MODES FOR PRACTICE OF THE INVENTION

EXAMPLE 1

2-Anilino-3-methyl-6-N-cyclohexylmethyl-N-ethylaminofluoran [Compound No. 1]:

To 175 g of 95% sulfuric acid was added 19.1 g of 2-hydroxy-4-N-cyclohexylmethyl-N-ethylamino-2'-carboxybenzophenone. While keeping at about 25° C., the mixture was completely dissolved. Thereafter 11.7 g of 2-methyl-4-methoxydiphenyl amine was added to the solution. The mixture was reacted at 0° to 5° C. for 20 hours and then at 30° C. for 24 hours. The reaction mixture was poured into 1 liter of ice water and an aqueous sodium hydroxide solution was then added to render pH 10 or more. The precipitates were collected by filtration. To the thus obtained cake were added 450 ml of toluene and 340 g of a 10% aqueous sodium hydroxide solution. After the mixture was stirred under reflux for 2 hours, the toluene layer was separated and washed with water. Toluene was removed by steam distillation. The precipitated crystals were collected by filtration. After the cake was washed with 200 ml of methanol, the crystals were collected again by filtration. The crystals were dried to obtain 21.7 g of pale yellow 2-anilino-3-methyl-6-N-cyclohexylmethyl-N-ethylaminofluoran. The fluoran compound showed a melting point of 166.0° to 168.5° C. Further the λ max in a 95% acetic acid solution and molecular extinction coefficient of the compound were 452 nm ($1.915 \times 10^4$) and 596 nm ($1.99 \times 10^4$), respectively. A solution of the compound in toluene was colorless but readily colored with silica gel to form a reddish black.

EXAMPLE 2

2-Anilino-3-chloro-6-N-cyclohexylmethyl-N-methylaminofluoran [Compound No. 2]:

To 175 g of 98% sulfuric acid was added 18.4 g of 2-hydroxy-4-N-cyclohexylmethyl-N-methylamino-2'-carboxybenzophenone. While keeping at about 25° C., the mixture was completely dissolved. Thereafter 12.3 g of 2-chloro-4-methoxydiphenylamine was added to the solution. The mixture was reacted at 10° to 20° C. for 48 hours. The reaction mixture was treated in a manner similar to Example 1 to obtain 19.3 g of pale yellow 2-anilino-3-chloro-6-N-cyclohexylmethyl-N-methylaminofluoran. The melting point of this compound was 155° to 157° C. A solution of the compound in toluene was colorless but readily colored with silica gel to form a black color.

EXAMPLE 3

2-Anilino-(2-chlorophenylamino)-6-N-cyclohexylmethyl-N-methylaminofluoran [Compound No. 3]:

To 175 g of 98% sulfuric acid was added 18.4 g of 2-hydroxy-4-N-cyclohexylmethyl-N-methylamino-2'-carboxybenzophenone. While keeping at about 25° C., the mixture was completely dissolved. Thereafter 12.3 g of 4-methoxy-2'-chlorodiphenylamine was added to the solution. The mixture was reacted at 10° to 20° C. for 48 hours. The reaction mixture was treated in a manner similar to Example 1 to obtain 21.5 g of pale yellow 2-anilino-2-chlorophenylamino)-6-N-cyclohexylmethyl-N-methylaminofluoran. The melting point of this compound was 186° to 188° C. A solution of the compound in toluene was colorless but readily colored with silica gel to form a reddish black color.

EXAMPLE 4

2-Anilino-3-methyl-6-N-β-cyclohexylethyl-N-methylaminofluoran [Compound No. 4]:

The reaction was carried out in a manner similar to Example 1 except that 19.1 g of 2-hydroxy-4-N-β-cyclohexylethyl-N-methylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 20.4 g of pale yellow 2-anilino-3-methyl-6-N-β-cyclohexylethyl-N-methylaminofluoran. The melting point of this compound was 190° to 192° C. A solution of the compound in toluene was colorless but readily colored with silica gel to form a reddish black color.

EXAMPLE 5

2-Anilino-3-methyl-6-N-cyclohexylmethyl-N-methylaminofluoran [Compound No. 5]:

The reaction was carried out in a manner similar to Example 1 except that 18.4 g of 2-hydroxy-4-N-cyclohexylmethyl-N-methylamino-2'-carboxybenzophenone was used in lieu of 19.1 g of 2-hydroxy-4N-cyclohexylmethyl-N-ethylamino-2'-carboxybenzophenone in Example 1. The reaction mixture was treated in a manner similar to Example 1 to obtain 21.7 g of pale yellow 2-anilino-3-methyl-6-N-cyclohexylmethyl-N-methylaminofluoran. The melting point of this compound was 198° to 200° C. A solution of the compound in toluene was colorless but readily colored with silica gel to form a reddish black color.

EXAMPLE 6

2-Anilino-3-methyl-6-N,N-dicyclohexylmethylaminofluoran [Compound No. 6]:

The reaction was carried out in a manner similar to Example 1 except that 22.5 g of 2-hydroxy-4-N,N-dicyclohexylmethylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 24.4 g of pale yellow 2-anilino-3-methyl-6-N,N-dicyclohexylmethylaminofluoran. The melting point of this compound was 208° to 211° C. A solution of the compound in toluene was colorless but readily colored with silica gel to form a reddish black color.

EXAMPLE 7

2-Anilino-3-methyl-6-N-β-cyclohexylethyl-N-cyclohexylaminofluoran [Compound No. 7]:

The reaction was carried out in a manner similar to Example 1 except that 22.5 g of 2-hydroxy-4-N-β-cyclohexylethyl-N-cyclohexylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 23.2 g of pale yellow 2-anilino-3-methyl-6-N-β-cyclohexylethyl-N-cyclohexylaminofluoran. The melting point of this compound was 206° to 208° C. A solution of the compound in toluene was colorless but readily colored with silica gel to form a reddish black color.

EXAMPLE 8

2-Anilino-3-methyl-6-N,N-di-β-cyclohexylethylaminofluoran [Compound No. 8]:

The reaction was carried out in a manner similar to Example 1 except that 23.9 g of 2-hydroxy-4-N,N-di-β-cyclohexylethylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 26.9 g of pale yellow 2-anilino-3-methyl-6-N,N-di-β-cyclohexylethylaminofluoran. The melting point of this compound was 173° to 176° C. A solution of the compound in toluene was colorless but readily colored with silica gel to form a reddish black color.

EXAMPLE 9

2-Anilino-3-methyl-6-N-cyclohexylmethyl-N-isopropylaminofluoran [Compound No. 11]:

The reaction was carried out in a manner similar to Example 1 except that 20.4 g of 2-hydroxy-4-N-cyclohexylmethyl-N-isopropylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 20.4 g of pale yellow 2-anilino-3-methyl-6-N-cyclohexylmethyl-N-isopropylaminofluoran. The melting point of this compound was 168° to 170° C. A solution of the compound in toluene was colorless but readily colored with silica gel to form a reddish black color.

EXAMPLE 10

2-Anilino-3-methyl-6-N-cyclohexylmethyl-N-n-butylaminofluoran [Compound No. 15]:

The reaction was carried out in a manner similar to Example 1 except that 20.5 g of 2-hydroxy-4-N-cyclohexylmethyl-N-n-butylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 19.3 g of pale brown 2-anilino-3-methyl-6-N-cyclohexylmethyl-N-n-butylaminofluorane. The melting point of this compound was 197° to 199° C. A solution of the compound in toluene was colorless but readily colored with silica gel to form a reddish black color.

EXAMPLE 11

2-Anilino-3-methyl-6-N-β-cyclohexylethyl-N-ethylaminofluoran [Compound No. 17]:

The reaction was carried out in a manner similar to Example 1 except that 19.8 g of 2-hydroxy-4-N-β-cyclohexylethyl-N-ethylamino-2'-carboxybenzophenone was used in lieu of 19.1 g of 2-hydroxy-4-N-cyclohexylmethyl-N-ethylamino-2'-carboxybenzophenone in Example 1. The reaction mixture was treated in a manner similar to Example 1 to obtain 21.5 g of pale yellow 2-anilino-3-methyl-6-N-β-cyclohexylethyl-N-ethylaminofluoran. The melting point of this compound was 197° to 199° C. A solution of the compound in toluene was colorless but readily colored with silica gel to form a reddish black color.

EXAMPLE 12

2-Anilino-3-chloro-6-N-β-cyclohexylethyl-N-ethylaminofluoran [Compound No. 18]:

The reaction was carried out in a manner similar to Example 1 except that 19.8 g of 2-hydroxy-4-N-β-cyclohexylethyl-N-ethylamino-2'-carboxybenzophenone and 12.3 g of 2-chloro-4-methoxydiphenylamine were used in lieu of 19.1 g of 2-hydroxy-4-N-cyclohexylmethyl-N-ethylamino-2'-carboxybenzophenone and 11.7 g of 2-methyl-4-methoxydiphenylamine in Example 1, respectively. The reaction mixture was treated in a manner similar to Example 1 to obtain 18.5 g of pale brown 2-anilino-3-chloro-6-N-β-cyclohexylethyl-N-ethylaminofluoran. The melting point of this compound was 188° to 190° C. A solution of the compound in toluene was colorless but readily colored with silica gel to form a black color.

EXAMPLE 13

2-Anilino-3-chloro-6-N,N-di-β-cyclohexylethylaminofluoran [Compound No. 19]:

The reaction was carried out in a manner similar to Example 1 except that 23.9 g of 2-hydroxy-4-N,N-di-β-cyclohexylethylamino-2'-carboxybenzophenone and 12.3 g of 2-chloro-4-methoxydiphenylamine were used in lieu of 19.1 g of 2-hydroxy-4-N-cyclohexylmethyl-N-ethylamino-2'-carboxybenzophenone and 11.7 g of 2-methyl-4-methoxydiphenylamine in Example 1, respectively. The reaction mixture was treated in a manner similar to Example 1 to obtain 20.4 g of pale brown 2-anilino-3-chloro-6-N,N-di-β-cyclohexylethylaminofluoran. The melting point of this compound was 170° to 172° C. A solution of the compound in toluene was colorless but readily colored with silica gel to form a black color.

EXAMPLE 14

2-(2-Chlorophenylamino)-6-N-cyclohexylmethyl-N-ispropylaminofluoran [Compound No. 21]:

The reaction was carried out in a manner similar to Example 1 except that 19.8 g of 2-hydroxy-4-N-cyclohexylmethyl-N-isopropylamino-2'-carboxybenzophenone and 12.3 g of 4-methoxy-2'-chlorodiphenylamine were used in lieu of 19.1 g of 2-hydroxy-4-N-cyclohexylmethyl-N-ethylamino-2'-carboxybenzophenone and 11.7 g of 2-methyl-4-methoxydiphenylamine in Example 1, respectively. The reaction mixture was treated in a manner similar to Example 1 to obtain 23.1 g of pale pink 2-(2-chlorophenylamino)-6-N-cyclohexylmethyl-N-ispropylaminofluoran. The melting point of this compound was 208° to 210° C. A solution of the compound in toluene was colorless but readily colored with silica gel to form a reddish black color.

EXAMPLE 15

2-Anilino-3-chloro-6-N-cyclohexylmethyl-N-ethylaminofluoran [Compound No. 22]:

The reaction was carried out in a manner similar to Example 1 except that 12.3 g of 2-chloro-4-methoxydiphenylamine was used in lieu of 11.7 g of 2-methyl-4-methoxydiphenylamine in Example 1. The reaction mixture was treated in a manner similar to Example 1 to obtain 18.2 g of pale brown 2-anilino-3-chloro-6-N-cyclohexylmethyl-N-ethylaminofluoran. The melting point of this compound was 158° to 160° C. A solution of the compound in toluene was colorless but readily colored with silica gel to form a reddish black color.

Next, a general method for preparing a heat-sensitive recording sheet using the fluoran compound of the present invention is shown below.

The fluoran compound, an acidic substance and a heat-meltable compound (this compound is used in case that the fluoran compound or the acidic substance does not melt at a preferred temperature) are finely divided and mixed with a solution or dispersion of a binder in a solvent or dispersion medium. The solution or dispersion is coated onto a support such as paper, a plastic sheet, a resin-coated paper sheet, etc. and dried to obtain the heat-sensitive recording sheet. Upon preparation of the solution mixture, all of the components may be mixed simultaneously and then finely divided; alternatively, they may be separately finely divided and dispersed and then mixed.

Proportions of the respective components constructing the heat-sensitive recording sheet are 1 part by weight of the fluoran compound, 2 to 10 parts by weight of the acidic substance, 0 to 10 parts by weight of the heat-meltable compound, 2 to 10 parts by weight of the binder and 50 to 150 parts by weight of the binder (dispersion medium).

It is preferred that the solvent (dispersion medium) scarcely dissolves both the fluoran compound and the acidic substance therein. As the solvent (dispersion medium) which can be used, water is most preferred; in addition, hydrocarbons such as hexane, ligroin, etc. are preferred.

Next, giving binders used in the present invention as examples, there are polyvinyl alcohol, hydroxyethyl cellulose, polyvinylpyrrolidone, styrene-maleic anhydride copolymers, etc.

As the heat-meltable substances, there may be used stearic amide, oleic amide, ethylenebis-stearoamide, benzenesulfoanilide, benzyloxyacetanilide, etc.

Next, the acidic substances which can be used in the present invention are those that have a property to form a color upon contact with the above-described fluoran compounds. Specific examples include 4-t-butylphenol, 4-phenylphenol, methyl-4-hydroxybenzoate, 4,4'-isopropylidenediphenol, 4,4'-idopropylidene(2,6-dibromophenol), bis(4-hydroxyphenyl)sulfone, benzyl p-hydroxybenzoate, sec-butyl p-hydroxybenzoate, 3-(α-methylbenzyl)salicylic acid, etc., which are known compounds. These acidic substances may be used in admixture of two or more.

To the coating solution, various coating aids may be added. Examples include dispersing agents such as sodium dioctylsulfosuccinate, sodium dodecylbenzenesulfonate, etc.; ultraviolet ray absorbers of benzophenone type, triazole type, etc.; defoaming agents, fluorescent dyes, coloring dyes, etc.

As the support, paper, a plastic film, synthetic paper, a woven sheet, etc. can be used; preferably paper is used. The amount coated on the support is not particularly limited but in the range of 2 to 15 g/m$^2$, preferably 3 to 10 g/m$^2$.

Hereafter, the present invention is explained with reference to the use examples of heat-sensitive recording sheets in which the fluoran compounds of the present invention are used.

The efficiency of the heat-sensitive recording sheet was examined by the following test method. That is, the background density was measured using Macbeth RD-514 Model reflection densitometer. Color formation upon heating was examined using Rodyaceta type thermotest tester (made by National Fiber Research Institute in France) under the conditions of a heating temperature of 60° to 170° C., a heating time for 3 seconds and a load of 100 g/m$^2$.

Use Example 1

Each of mixtures having compositions described below was separately pulverized for 3 hours using a paint conditioner (trademark, Red Devil) to prepare Liquid (A), Liquid (B) and Liquid (C).

| Composition of Liquid (A): | |
|---|---|
| 2-Anilino-3-methyl-6-N—cyclohexylmethyl-N—ethyl-aminofluoran [Compound No. 1] | 4 parts by weight |
| 1090 Polyvinyl alcohol aqueous solution | 34 parts by weight |
| 5% Defoaming agent (San Nopco 1407, made by San Nopco Co.) | 2 parts by weight |
| Composition of Liquid (B): | |
| Bisphenol A | 6 parts by weight |
| 10% Polyvinyl alcohol aqueous solution | 20 parts by weight |
| Water | 14 parts by weight |
| Composition of Liquid (C): | |
| Aluminum hydroxide | 10 parts by weight |
| 10% Polyvinyl alcohol aqueous solution | 20 parts by weight |
| Water | 10 parts by weight |

Liquid (A), Liquid (B), Liquid (C) and water were mixed in a weight ratio of 3:9:5:3 to obtain a coating composition for a heat-sensitive recording sheet. The coating solution was coated onto the surface of a high quality paper sheet in a dry solid weight of 5 g/m$^2$ using a wire bar, put in a air drier to dry at room temperature. Heat-sensitive recording sheet (a) in accordance with the present invention was obtained.

Comparative Example 1

Heat-sensitive recording sheet (p) for comparison was obtained in a manner similar to Use Example 1 except that Liquid (D) was used in lieu of Liquid (A).

| Composition of Liquid (D): | |
|---|---|
| 2-Anilino-3-methyl-6-N—methyl-N—cyclohexylamino-fluoran | 4 parts by weight |
| 10% Polyvinyl alcohol aqueous solution | 34 parts by weight |
| 5% Defoaming agent (San Nopco 1407) | 2 parts by weight |

The thus obtained heat-sensitive recording sheet in accordance with the present invention and the heat-sensitive recording sheet for comparison were examined with respect to color sensitivity and background fogging.

Use Example 2

Heat-sensitive recording sheets (b) through (o) were obtained in a manner similar to Use Example 1 except that the fluoran compounds shown in the following Table 1 were used instead of [Compound No. 1] used in Use Example 1. The efficiency of the heat-sensitive recording sheets in accordance with the present invention was tested in a manner similar to Use Example 1. The results are shown in Table 1.

TABLE 1

| | Heat-Sensitive Recording Sheet No. | Fluoroan Compound of General Formula (I) | | | | Background Density$^{(1)}$ | Color Sensitivity $T_{1.0}^{(2)}$ |
|---|---|---|---|---|---|---|---|
| | | $R_1$ | $R_2$ | $R_3$ | n | | |
| Use Example 1 | a | $C_2H_5$ | $CH_3$ | H | 1 | 0.12 | 115 |
| Use Example 2 | b | $C_2H_4$—⟨H⟩(cyclohexyl) | $CH_3$ | H | 2 | 0.12 | 115 |
| | c | $CH_3$ | Cl | H | 1 | 0.09 | 119 |
| | d | $CH_3$ | $CH_3$ | H | 2 | 0.07 | 120 |
| | e | $CH_3$ | $CH_3$ | H | 1 | 0.20 | 119 |
| | f | ⟨H⟩(cyclohexyl) | $CH_3$ | H | 2 | 0.13 | 117 |
| | g | $C_2H_5$ | H | O—Cl | 1 | 0.10 | 120 |
| | h | $C_4H_9(n)$ | $C_2H_4OC_2H_5$ | H | 2 | 0.12 | 114 |
| | i | $C_2H_5$ | $CH_2$—⟨phenyl⟩ | H | 1 | 0.09 | 120 |
| | j | $CH(CH_3)_2$ | $CH_3$ | H | 1 | 0.15 | 113 |
| | k | $CH(CH_3)_2$ | Cl | H | 2 | 0.11 | 118 |
| | l | $C_2H_5$ | H | H | 1 | 0.13 | 115 |
| | m | $CH_3$ | ⟨phenyl⟩ | H | 1 | 0.13 | 119 |

TABLE 1-continued

| Heat-Sensitive Recording Sheet No. | Fluoroan Compound of General Formula (I) | | | | Background Density[1] | Color Sensitivity $T_{1.0}$[2] |
|---|---|---|---|---|---|---|
| | $R_1$ | $R_2$ | $R_3$ | n | | |
| n | −CH$_2$−⟨phenyl⟩ | CH$_3$ | H | 1 | 0.09 | 121 |
| o | −CH$_2$−CH$_2$−CH(CH$_3$)$_2$ | −CH$_2$OC$_2$H$_5$ | H | 1 | 0.16 | 118 |
| Comparative Example 1 p | 2-Anilino-3-methyl-6-N—cyclohexyl-N—methylaminofluoran | | | | 0.39 | 127 |

[1]Density at the white areas in a state that the heat-sensitive color forming layer is not colored.
[2]Heating temperature when a color density is 1.0; the lower the temperature, the better the color sensitivity The heat-sensitive recording sheets in which the fluoran compounds of the present invention are used provided a minimized density at the background and extremely excellent color sensitivity, particularly excellent color sensitivity as compared to the heat-sensitive recording sheet for comparison; and were of sufficiently practical value as heat-sensitive recording sheets in various recording fields, particularly for high speed recording.

We claim:

1. A fluoran compound represented by the general formula (I):

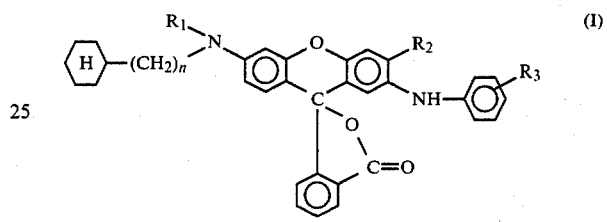

wherein $R_1$ represents a cyclohexyl ($C_1$–$C_2$) alkyl group; $R_2$ represents a hydrogen atom, a halogen atom, a lower alkyl group having 1 to 4 carbon atoms; $R_3$ represents a hydrogen atom, a chlorine atom, a fluorine atom or a lower alkyl group having 1 to 4 carbon atoms; and n is 2.

2. A compound according to claim 1, which is 2-anilino-3-methyl-6-N,N-di-β-cyclohexylethylaminofluoran.

3. A compound according to claim 1, which is 2-anilino-3-chloro-6-N,N-di-β-cyclohexylethylaminofluoran.

* * * * *